United States Patent [19]

Peacock et al.

[11] Patent Number: 4,534,225
[45] Date of Patent: Aug. 13, 1985

[54] METHOD AND APPARATUS FOR SUPPORTING CYLINDRICAL CONCRETE SAMPLES FOR TESTING

[75] Inventors: Bobbie D. Peacock; John N. Mushovic; Roger D. Geyer, all of Peachtree City, Ga.

[73] Assignee: M. A. Industries, Inc., Peachtree City, Ga.

[21] Appl. No.: 519,068

[22] Filed: Aug. 1, 1983

[51] Int. Cl.$^3$ .............................................. G01N 3/02
[52] U.S. Cl. ...................................... 73/860; 73/818; 73/864.91; 248/632
[58] Field of Search ................. 73/11, 818, 856, 860, 73/863, 864.91; 173/139; 248/562, 632, 633

[56] References Cited

U.S. PATENT DOCUMENTS 3,153,929 10/1964 Baldwin ............................... 73/856
4,174,625 11/1979 Milberger et al. ...................... 73/11

FOREIGN PATENT DOCUMENTS 2398297 3/1979 France ................................. 73/818
0905708 2/1982 U.S.S.R. ............................... 73/818

Primary Examiner—S. Clement Swisher
Attorney, Agent, or Firm—Patrick F. Henry

[57] ABSTRACT

A method and apparatus for supporting concrete testing samples comprising providing closely machined aluminum, steel, or suitable molded plastic caps for the respective circular ends of a cylindrical concrete testing sample and removable, reusable flanged molded elastomeric pads which are inserted in a recessed cavity in each cap prior to positioning of the cap on the respective end of the concrete cylinder. Each pad has a space between the bottom and the side to provide at least an equivalency between sulfur capped cylinder compression load strengths and those generated by the above system over the wide range of compression load values normally occurring in this particular test.

17 Claims, 9 Drawing Figures

METHOD AND APPARATUS FOR SUPPORTING CYLINDRICAL CONCRETE SAMPLES FOR TESTING

BACKGROUND OF THE INVENTION

1. Field of the Invention

Concrete sample testing and support means therefor comprising end caps and removable molded elastomeric insert pads for positioning over the ends of the cylindrical concrete sample.

2. Description of the Prior Method and Apparatus

In the prior practice concrete samples are obtained from a job site by pouring a small quantity of the concrete into a cylindrical plastic container which subsequently is stripped away prior to placing the cylindrical concrete sample in a testing machine which ordinarily included compressing the cylindrical sample until it cracked or broke at a certain pressure. In order to properly place and align the individual cylindrical concrete samples in the testing machines, it was necessary first to provide a special surface on each end of the concrete cylinder which was usually done by heating ordinary sulphur to the ends of the cylinder by using a special mold which was removed after the sulphur cooled and hardened. This was a hot, dirty and somewhat dangerous procedure which, among other things, required a quantity of heated sulphur to be maintained at all times and besides the danger of the hot sulphur there is a most disagreeable odor and fumes about the premises. There is also a prior procedure mentioned in Research Report 46 (Report N.Y.S. DOT-ERD-77 RR46) Engineering Research and Development Bureau, New York State Department of Transportation "CAPPING CONCRETE CYLINDERS WITH NEOPRENE PADS" in which flat neoprene pads (similar to FIGS. 6 and 7 herein), were used in extrusion controllers in comparison with sulphur-mortar caps.

SUMMARY, OBJECTS AND ADVANTAGES

In preparing cylindrical concrete samples for subsequent testing insert the method and procedure of the present invention comprises providing circular end caps on each end of the concrete sample and a removable elastomeric (e.g. plastic) pad removably inserted in a cavity in each end cap so that the bottom surface and inner wall of the end cap is positioned against the elastomeric insert pad. The caps may be machined from steel, aluminum, or molded plastic in circular form with a circular cavity on one side thereof which is significantly larger in diameter than the overall diameter of the cylindrical concrete testing sample. The flanged insert pad is slightly larger in diameter than the overall diameter of the cavity in the end cap so that the pad may be inserted tightly therein for removal therefrom and there is a space, groove or gap in the pad next to the outside wall spacing at least part of the bottom from the side wall.

An advantage of this invention resides in the use of reusable end caps and reusable pads rather than substances such as liquid sulphur applied directly to the ends of the cylindrical testing samples or neoprene pads that are more quickly ruined.

Another object of this invention is found in the use of a machined metal cap with the diameter of the recessed cavity much larger than that normally expected for a given size of cylinder. When used with a flanged, molded elastomeric insertable and tightly fitted pad, the following advantages accrue.

(1) Extrusion of the elastomer is more uniform, resulting in a more uniform load applied during loading which in turn results in compressive stress results more truly representing that of the cylinder.

(2) Less edge chipping of the cylinder under load since forces are uniformly distributed around the cylinder's periphery which in turn eliminates sudden compressive stress changes on the cylinder which in turn results in compressive stress values more truly representing the cylinder.

(3) Since the total lateral movement of the cylinder in the present system is controlled to less than 0.050 inches, centering the cylinder in the test machine is facilitated and cylinder tilt is minimized, thereby insuring uniform load application, thereby generating compressive load values more truly representing that of the cylinder.

(4) When compared to systems using the flat pads (e.g. neoprene), and since the recessed cavity in the caps must be machined to compensate for cylinder ovality at the expense of extrusion control, it is likely that flat pad extrusion is not consistently uniform, compression loads may not be as uniformly applied and compressive stress values may not truly represent that of the cylinder.

(5) When compared to systems using the flat pads (e.g. neoprene), and since the recessed cavity in the caps must be machined to compensate for cylinder ovality, potential lateral movement of the cylinder in the cap allows the possibility of assembling the cylinder tilted in the test machine which would generate nonuniform load distribution over the compression surfaces of the cylinder with resultant compressive stress values which may not truly represent that of the cylinder.

Another object of this invention is found in the surface preparation of the pad, whereby manufacturing oils are removed from the pads surface through the use of a suitable detergent and water above 150° F., thereby further controlling the extrusion of the pad under a wide load range, thereby generating more uniform loading during compression, which in turn results in a compressive stress value more truly representing that of the cylinder.

Another object of this invention is found in the surface preparation of the machined metal cap whereby cutting oils are removed by a suitable solvent and the surface of the recessed cavity effectively roughened by the addition of a suitable grit or by sandblasting. The surface preparation acts to control extrusion over a wider load range thereby insuring uniform loading of the cylinder over a wide load range thereby generating compressive stress values more truly representing that of the cylinders.

Another object of this invention is found in the physical properties of the pad material in conjunction with the controlled measurements of both the elastomeric flanged pad and the machined metal cap.

Another object of this invention is found within the balance of flanged pad properties and design and the cap recessed cavity design and surface preparation whereby the overall system is useful for generating uniform loads on cylinders representing a wide range of stress values thereby making it unnecessary to employ material or design changes for testing concrete cylinders, each of which may have a significantly different compressive stress value.

Other and further objects and advantages of this invention will become apparent upon reading the following description of a preferred method and embodiment taken in conjunction with the accompanying drawings.

DESCRIPTION OF A PREFERRED METHOD AND EMBODIMENT

Figure 1:
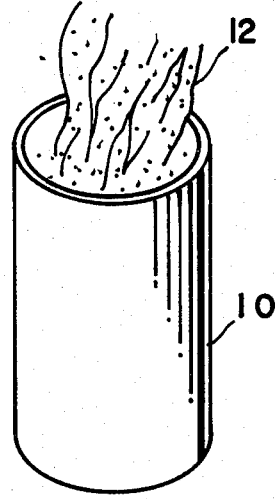
FIG. 1 is a perspective view of a prior art plastic container receiving a quantity of poured concrete therein.
Figure 2:
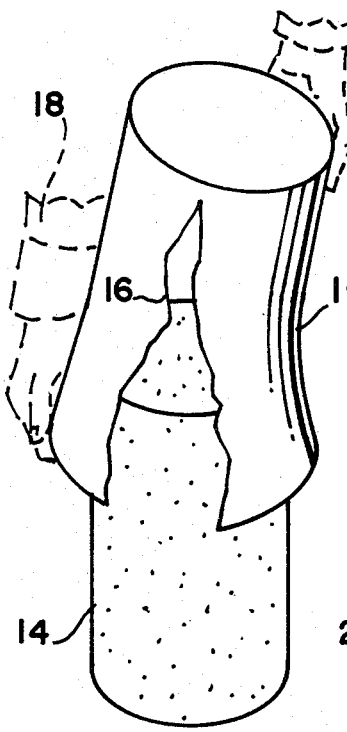
FIG. 2 is a perspective view of the plastic container being stripped from the solidified and hardened concrete sample.

In FIG. 1 a conventional plastic concrete container 10 receives a quantity of poured concrete 12 for testing purposes. The poured concrete 12 is a sample to be tested in the laboratory to determine whether the concrete is according to specification on the job or the particular characteristics of the sample. One of the main tests is to compress the sample poured concrete 12 in a testing machine (not shown) to compress the sample which has solidified and is shown as a solid cylindrical concrete sample 14 in FIG. 2. The container 10 is stripped away from the sample cylinder 14 in a conventional manner by any suitable method such as cutting along lines 16 and removing by hands 18 as shown in FIG. 2. The foregoing method and apparatus is generally well known in the prior art wherein after stripping from the container 10 the sample cylinder 14 is provided with flat surfaces on each end of the concrete so that the cylinder 14 could properly be tested in the machine as it was not possible to perform proper testing without some kind of surfaces on the end of the concrete cylinder 14. Usually this is done by heating ordinary sulphur to about 350° F. and then inserting the respective ends of a cylinder 14 in the liquid sulphur in a temporary mold or some other container thereafter cooling and solidifying the sulphur to provide a surface of some thickness on the end of the cylinder 14. This procedure was not without some amount of hazard and danger because of the hot liquid sulphur and furthermore it was dirty and awkward and the sulphur caused an obnoxious stink in the work area. Of course, the sulphur surfaces are destroyed when the concrete cylinder 14 is put through the testing procedure and hard sulphur surfaces have to be provided on each cylinder.

Figure 6:
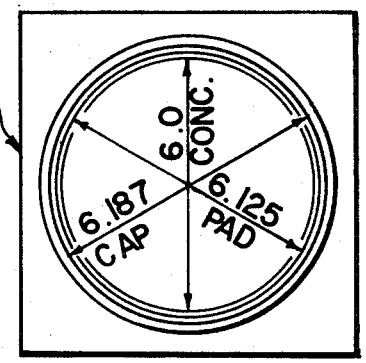
FIG. 6 is a top plan diagrammatic comparison of the previously mentioned flat pad system with the present molded pad system showing potential lateral movement.
Figure 7:
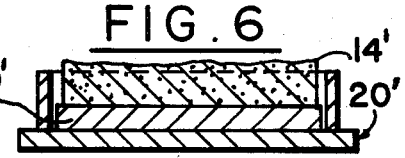
FIG. 7 is a section view of the system shown in FIG. 6.
Figure 8:
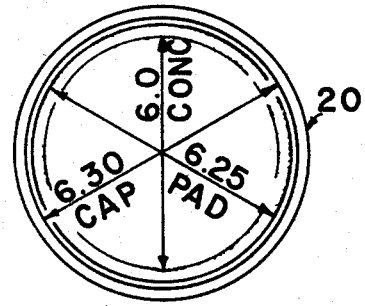
FIG. 8 is a top plan diagrammatic view of the present device in FIGS. 4 and 5 illustrating dimensional and other relationship.
Figure 9:
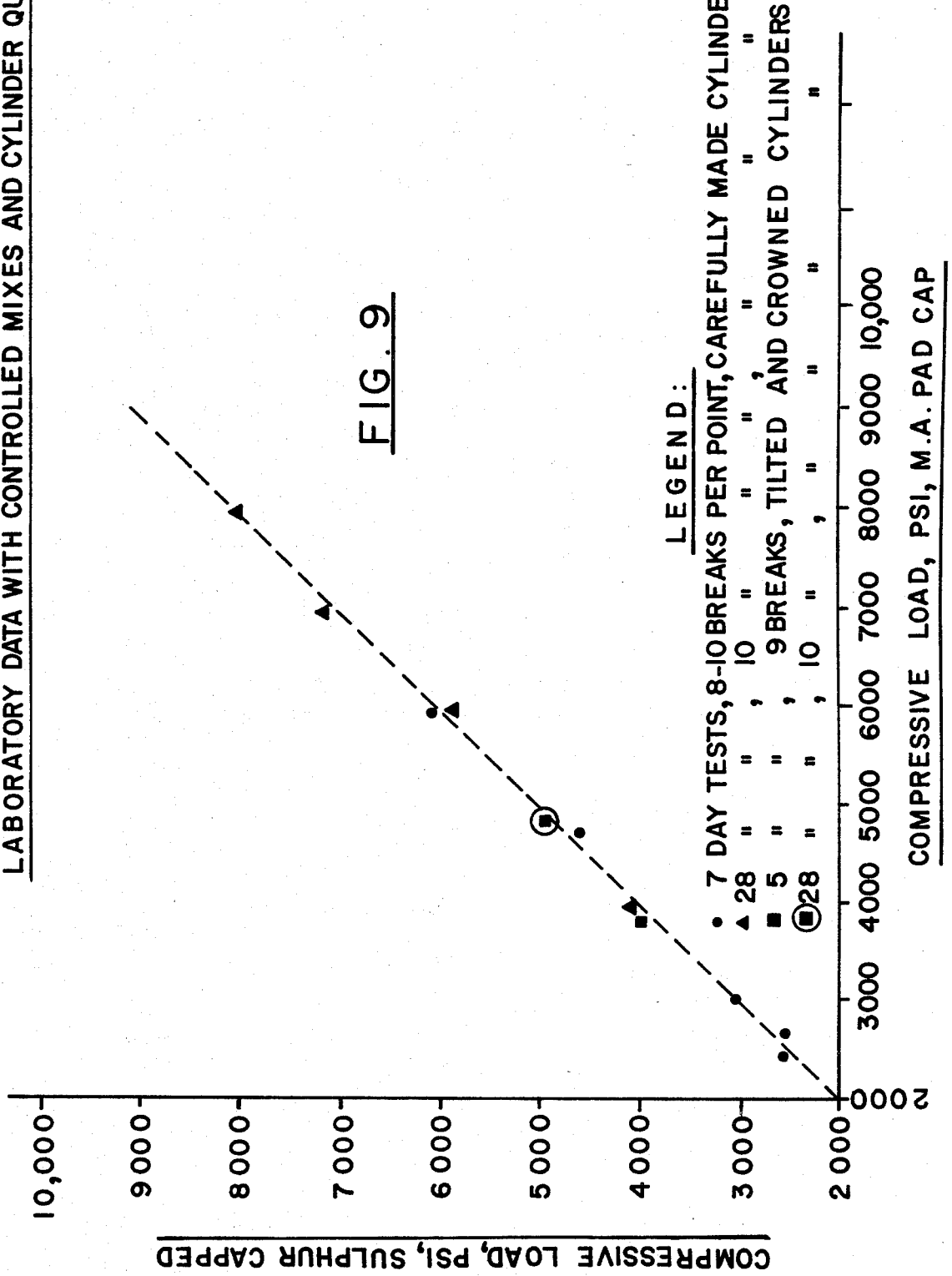
FIG. 9 is a graph showing agreement and measured range between cylinders tested using sulphur and cylinders tested using the present method and apparatus designated M. A. "PAD CAP" (trademark).

As mentioned previously there is also a prior procedure shown in FIGS. 6 and 7 using flat pads.

Figure 3:
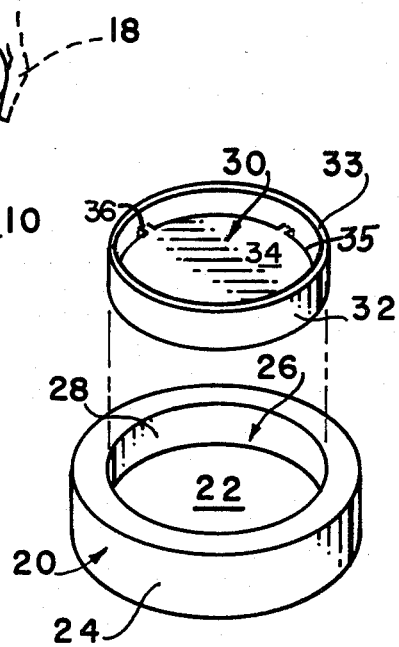
FIG. 3 is a perspective view of a disassembled end cap and removable pad of the present invention.
Figure 4:
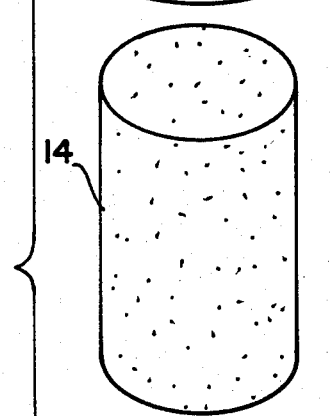
FIG. 4 is a disassembled assembly view of the respective end caps and the concrete sample.

According to the present procedure and apparatus, as seen in FIGS. 3 and 4, the concrete cylinder 14 is provided with temporary and removable reusable machined metal caps 20 each comprising a flat cap top 22 and a circular or flange rim 24 which defines with the inside bottom of the top 22 a cavity 26 which has a cavity wall 28 on the inside flange 24. As seen in FIG. 3, there is positioned in cavity 26 next to wall 28 a flanged elastomeric pad 30 having a smooth outer annular and circumferential edge 32 and a flange 33 which in total depth and thickness are of less thickness than the depth of the wall 28 of cavity 26 so that when the molded pad 30 is assembled into the cavity 26 there is a space in the recess of molded pad 30 surrounded by flange 33 which receives one end of the concrete cylinder 14 in the manner shown in FIG. 4. Pad 30 has a circular flat top 34 which is recessed below flange 33 and against which the top and bottom respectively of of cylinder 14 are positioned for testing (see FIG. 5). Bottom 34 is separated from flange 33 by an annular circular groove or channel 35 connected to flange 33 by small web members 36 at spaced locations (see FIG. 3). The entire pad may be molded, for example, from a polyurethane elastomer comprised of a polyester or polyether based resin, and a diisocyanate chosen from the group consisting of 2,4-toluene diisocyanate and mixtures of this with 2,6-toluene diisocyanate (TDI), 4,4-diphenyl methane diisocyanate (MD1), polymethylene polyphenyl isocyanate, 1,5 naphthalene diisocyanate (ND1), 1,6-hexamethylene diisocyanate (HD1), 4,4-dicyclohexylmethane diisocyanate ($H_{12}MD1$), xylene diisocyanate, and isophorone diisocyanate.

In formulating the elastomer from which the pad is made, various curing agents for the urethane may be employed, including low molecular weight diols, ethylene glycol, diethylene glycol and 1,4 butanediol or low molecular weight triols such as trimethylol propane and mixtures thereof. For example, a blend or mixture of a low molecular weight triol such as trimethylol propane and a low molecular weight diol such as 1,4 butanediol may be employed. The amount of the triol may be from about 1 to 99 weight % of the mixture. A preferred blend would include 1,4 butanediol in an amount of about 60 to 80 weight % and trimethylol propane in an amount of about 20 to 40 weight %. This mixture would be used to chain extend and crosslink the urethane. The amount of the mixture to be employed would be a function of the percent free NCO of the urethane. As a further example, the triol triisopropanolamine (T.I.P.A.) may be employed alone to chain extend and crosslink the urethane prepolymer in order to manufacture a suitable pad.

Figure 5:
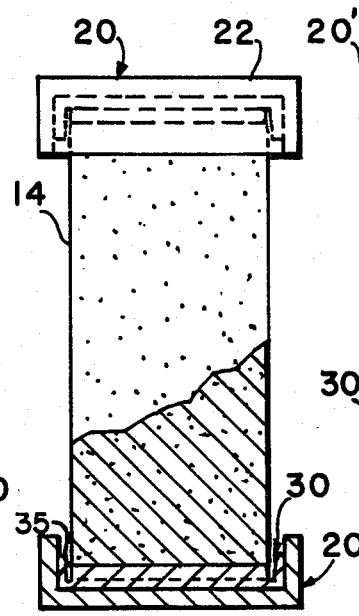
FIG. 5 is a side elevation view of the concrete sample supported by the present invention for testing.

In the manner shown in FIG. 4 the concrete cylinder 14 is provided with respective end caps 20 each having a respective molded elastomeric pad 30 therein for temporary assembly in the manner shown in FIG. 5 and insertion into a testing machine (not shown) so that the concrete cylinder 14 is compressed in the machine between caps 20 until it breaks or fractures after which the end caps 20 and the molded elastomeric pads 30 are removed, if indeed the ends of the concrete cylinder 14 are still inside the end caps 20 after crushing or fracturing. End caps 20 and the molded elastomeric pads 30 may be reused any number of times until and if same become so worn or broken that they are no longer properly usable. Molded elastomeric pad 30 is no longer usable when the flange 33 loses more than 50% of its periphery and will not center the cylinder 14 of the end cap recess 26.

Caps 20 are machined to required dimensions. The inside dimension of end cap 20, for example, is 6.3 inches in diameter and the depth of the wall 28 of cavity 26 is 1.25 inches overall. The overall thickness of the molded elastomeric pad 30 bottom 34 should be greater than 0.6875 inches and is normally 0.750 inches. The flange 33 of the molded elastomeric pad 30 has an approximate height of 0.250 inches above the bottom 34. The total lateral movement of the cylinder 14 in the cap 20 is less than 0.050 inches. As seen in FIGS. 6 and 7, the prior form cap 20' has an internal diameter of approximately 6.187 and the pad 30' a diameter of approximately 6.125 so there is a tolerance of about 0.062 between cap 20' and pad 30' and the inside of top 20'. The concrete sample 14 or top of pad 30' in FIGS. 6 and 7 is about 6.00 inches in diameter so there is about 0.125 inches of difference and tolerance which is apparent in FIG. 7 in the space between cap 30 and the concrete sample 14. Unlike the prior device pad 30', the present pad 30 has the gap or space in the groove 35 which spaces the outside of cylinder 14 from the flange 33 but the bottom 34 of pad 30 is about the same size or the diameter of the concrete sample 14.

Within the constraints of the design parameters, it was found that the following properties were useful for generating the controlled extrusion in the pad 30 necessary for uniform load application on the cylinder 14 over a wide load range whereby the measured compressive stress values more truly represented that of the cylinder.

Typical properties are as follows:

| | |
|---|---|
| Tensile strength | >3000 psi |
| Shore A Hardness | 52–60 Shore A |
| Split Tear | >15 pli |
| Elongation | 200° |
| Rebound | 25–40% |
| Permanent Set | 10% |

The preceding properties are for the preferred embodiment. Any elastomer with acceptable properties can be used. An elastomer is a synthetic or natural material, modified or unmodified, which at room temperature can be stressed to 200% of its length and will return substantially to its original length when the stress is released. This term applies to most rubber material and to some rubber-modified plastics.

Acceptable material for this invention have typical elastomeric properties as follows:

| | | ASTM |
|---|---|---|
| Tensile Strength | 1,000–5,000 psi | D412 |
| Hardness | 52–60 Shore A | D2240 |
| Split Tear | >15 pli | D1938 |
| Elongation | At least 200% | D412 |
| Rebound | Min. 15–50% | |
| Permanent Set | <15% | D412 |

While we have shown and described a particular method and apparatus by way of a preferred procedure and embodiment this is not to be construed as any sort of limitation on the scope of the invention because there are various alterations, changes, deviations, departures and revisions which may be made in the method and apparatus without departing from the scope of the invention as defined by a proper interpretation of the appended claims.

What is claimed:

1. In a flexible elastomeric pad for insertion in respective cavities of each of the opposed caps which are fitted at opposite ends of a concrete test sample, comprising:
a pad bottom surrounded by a peripheral side wall extending upwardly therefrom defining an open cavity in said pad for receiving one end of the concrete sample therein, the top of the pad bottom which receives the concrete flat end thereagainst being recessed and below the upper edge of the outer side wall whereby the side wall extends around the end of the concrete sample, said overall width and dimension of said pad being such that the pad is tightly fitted into the cavity of the cap so that the outside of the side wall is in contact with the inside of the cap, a recessed top on the bottom of said pad whereby the top of the bottom is below the side wall, said bottom being spaced from said side wall defining a depression between said side wall and said bottom, the pad bottom and end of the cylinder being about the same size but the inside of the cap being larger than the pad bottom.

2. The device claimed in claim 1 wherein there are connecting members at spaced locations between the bottom of said pad and the side wall of said pad and extending across the space therebetween.

3. The device claimed in claim 1 wherein said concrete cylinder, said end caps and said pad are circular in construction and said side wall of said pad is an annular circumferential side wall separated by an annular circumferential groove between said side wall and the bottom of said pad.

4. The device in claim 3 wherein the inside diameter of the cap is approximately 6.30 inches and the outside of the pad about the same, the end of the concrete and the top of the bottom of the pad about 6.0 inches, and the diameter of the inside of the side wall of the pad about 6.25 inches inclusive of the space between the side wall and the pad bottom.

5. The pad in claim 1 having the following approximate elastomeric properties:

| | | ASTM |
|---|---|---|
| Tensile Strength | 1,000–5,000 psi | D412 |
| Hardness | 52–60 Shore A | D2240 |
| Split Tear | >15 pli | D1938 |
| Elongation | At least 200% | D412 |
| Rebound | Min. 15–50% | |
| Permanent Set | <15% | D412 |

6. The pad in claim 1 having the following approximate properties:

| | |
|---|---|
| Tensile Strength | >3,000 |
| Hardness | 52–60 Shore A |
| Split Tear | >15 pli |
| Elongation | 200% |
| Rebound | 25–40% |
| Permanent Set | 10% |

7. The pad in claim 1 wherein the pad is constructed from a polyurethane elastomer material of a polyester or polyether based resin, and a diisocyanate chosen from the group consisting of 2,4-toluene diisocyanate and mixtures of this with 2,6-toluene diisocyanate (TDI), 4,4-diphenyl methane diisocyanate (MDI), polymethylene polyphenyl isocyanate, 1,5 naphthalene diisocyanate (NDI), 1,6-hexamethylene diisocyanate (HDI), 4,4-dicychlohexylmethane diisocyanate ($H_{12}$MDI), xylene diisocyanate, and isophorone diisocyanate.

8. The pad in claim 7 wherein the material comprises a polyester based resin and 2,4 and 2,6-Toluene diisocyanate.

9. The pad in claim 8 wherein the urethane is cured by using curatives such as low molecular weight diols, ethylene glycol, diethylene glycol and 1,4 Butanidiol or low molecular weight triols such as trimethylol propane and mixtures thereof.

10. The pad in claim 9 wherein the material is cured with a low molecular weight triol.

11. In a flexible elastomeric pad for insertion in respective cavities of each of the opposed caps which are fitted at opposite ends of a concrete test sample, comprising:

a pad bottom surrounded by a peripheral side wall extending upwardly therefrom defining an open cavity in said pad for receiving one end of the concrete sample therein, the top of the pad bottom which receives the concrete flat end thereagainst being recessed and below the upper edge of the outer side wall whereby the side wall extends around the end of the concrete sample, said overall width and dimension of said pad being such that the pad is tightly fitted into the cavity of the cap so that the outside of the side wall is in contact with the inside of the cap, said pad having the following properties:

|  |  | ASTM |
|---|---|---|
| Tensile Strength | 1,000–5,000 psi | D412 |
| Hardness | 52–60 Shore A | D2240 |
| Split Tear | >15 pli | D1938 |
| Elongation | At least 200% | D412 |
| Rebound | Min. 15–50% |  |
| Permanent Set | <15% | D412 |

12. The pad in claim 11 having the following properties:

| Tensile Strength | >3,000 |
|---|---|
| Hardness | 52–60 Shore A |
| Split Tear | >15 pli |
| Elongation | 200% |
| Rebound | 25–40% |
| Permanent Set | 10% |

13. The pad in claim 11 wherein the material in the pad is a polyurethane elastomer composed of a polyester or polyether based resin, and a diisocyanate chosen from the group consisting of 2,4-toluene diisocyanate and mixtures of this with 2,6-toluene diisocyanate (TDI), 4,4-diphenyl methane diisocyanate (MDI), polymethylene polyphenyl isocyanate, 1,5 naphthalene diisocyanate (NDI), 1,6-hexamethylene diisocyanate (HDI), 4,4-cyclohexylmethane diisocyanate ($H_{12}$MDI), xylene diisocyanate, and isophorone diisocyanate.

14. The pad in claim 13 wherein the material comprises a polyester based resin and 2,4 and 2,6-Toluene diisocyanate.

15. The pad in claim 11 wherein the material comprises a polyester based resin and 2,4 and 2,6-Toluene diisocyanate.

16. The pad in claim 13 wherein urethane is cured by using curatives such as low molecular weight diols, ethylene glycol, diethylene glycol and 1,4 Butanidiol or low molecular weight triols such as trimethylol propane and mixtures thereof.

17. The pad in claim 16 wherein the material is cured with a low molecular weight triol.

* * * * *